United States Patent [19]

Janssen et al.

[11] 4,306,860
[45] Dec. 22, 1981

[54] MOUNT FOR ARTIFICIAL TEETH

[75] Inventors: Hansjorg J. Janssen, Constance; Karl-Heinz Meislitzer, Wiesbaden, both of Fed. Rep. of Germany

[73] Assignee: Dentsply Research & Development Corp., Milford, Del.

[21] Appl. No.: 198,895

[22] Filed: Oct. 20, 1980

[30] Foreign Application Priority Data

Nov. 22, 1979 [DE] Fed. Rep. of Germany ....... 2947094

[51] Int. Cl.³ ............................................. A61C 19/10
[52] U.S. Cl. ....................................... 433/26; 206/460
[58] Field of Search ................... 433/26, 163; 206/83, 206/460; 249/54

[56] References Cited

U.S. PATENT DOCUMENTS

| D. 150,509 | 8/1948 | Myerson | 206/83 |
|---|---|---|---|
| 1,502,366 | 7/1924 | Wright | 433/34 |
| 1,658,936 | 2/1928 | Myerson | 206/83 |
| 1,857,714 | 5/1932 | Evans | 206/83 |
| 2,341,153 | 2/1944 | Myerson | 433/26 |
| 2,363,977 | 11/1944 | Rothman | 206/83 |
| 2,889,598 | 6/1959 | Lundquist et al. | 249/54 |
| 3,018,884 | 1/1962 | Fritz | 433/26 |
| 3,414,093 | 12/1968 | Chostner | 206/460 |

FOREIGN PATENT DOCUMENTS

| 7403850 | 2/1974 | Fed. Rep. of Germany | 433/26 |
|---|---|---|---|
| 1044241 | 11/1953 | France | 433/26 |
| 462559 | 3/1951 | Italy | 433/26 |
| 566518 | 1/1945 | United Kingdom | 249/54 |
| 621006 | 4/1949 | United Kingdom | 206/460 |

*Primary Examiner*—Gene Mancene
*Assistant Examiner*—John J. Wilson
*Attorney, Agent, or Firm*—C. Hercus Just

[57] ABSTRACT

A mount for holding a set of artificial teeth comprising an elongated plate member having a row of recesses therein complementary to the lingual surfaces of said teeth and having adhesive in shallow indentations in the bottoms of said recesses to detachably secure the teeth therein and support them in such manner that the outer surfaces of the teeth are sloped forwardly for viewing.

4 Claims, 6 Drawing Figures

MOUNT FOR ARTIFICIAL TEETH

BACKGROUND OF THE INVENTION

This invention relates to a mount for artificial teeth, commonly known as a tooth card, and operative to support a set of teeth in a row for detachable connection thereto and particularly adapted for display purposes, as well as maintaining the teeth in an orderly manner during storage.

Mounts or cards of this type are well-known and have been used for many years. They have been used to support both anterior and/or posterior teeth, formed either of porcelain or plastic material, and have been employed ever since the dental profession first engaged in the manufacture and sale of prefabricated artificial teeth, in order that such teeth could conveniently be displayed by dental dealers or dentists and dental technicians in a safe and faultless manner for selection of the teeth, as well as for storage thereof, said teeth being readily removable from said mounts or cards when the same were to be used, such as by a dentist or dental technician to include them in a denture.

Mounts of the type referred to have heretofore been made of various materials, such as wood, metal, plastic material or the like, and have ranged from opaque to transparent material which could be pigmented and the design thereof has varied, depending upon the intended use of the artificial teeth, such as for use in dentures or crown and bridge work.

For example, transparent cards from plastic material have been known to card a set of anterior teeth, consisting of two each of central teeth, lateral incisors, and cuspids, while in another design, dimensions of the card from such transparent plastic material were such that porcelain or plastic posterior teeth for both the right and left-hand upper or lower sides of the jaw could be mounted thereon.

According to a further design, it has been known to attach the artificial teeth individually, or as pairs, to relatively short cards and to combine such single or pairs of teeth mounted upon such short cards in assembly with other short cards of complementary teeth to form sets thereof by means of attaching the same to a special carrying member, such as a strip or band, as in U.S. Pat. No. 3,018,884 to Fritz, dated Jan. 20, 1962.

One important feature of the mounts or cards used heretofore is that the card was provided with a recess of several millimeters in width located approximately in the center of the card between the upper and lower edges, running parallel to the longitudinal axis, and this is filled with a soft wax, such as rose-pink in color, and the wax serves as the actual means of adhering the teeth to the tooth card incident to mounting the teeth upon the card in a process referred to as "carding". One type of card of this type is illustrated in prior U.S. Pat. No. 1,658,936 to Myerson, dated Feb. 14, 1928, and in which several examples of recesses for holding such strips of wax are shown.

To afford better judging of the shade features of artificial teeth, other designs of cards have become known that are provided with a small cleft or recess in that part of the card that accommodates the incisal areas of the anterior teeth mounted thereon.

The types of cards now known and referred to hereinabove for supporting artificial teeth have not proven unduly satisfactory, even though they have been known and used for many years because the optical and aesthetic evaluation possibilities afforded by such previously used cards cannot be fully realized and, further, the known disadvantage of the use of wax for adhering the artificial teeth incident to removing the same from the tooth card, comprises an inconvenience which must be overcome by removing such adhering, undesired particles of wax from the teeth before they can be employed in dental restorative techniques.

In order to eliminate certain of the disadvantages set forth above relative to using wax strips for adhering artificial teeth on tooth cards, German Gebrauchsmuster No. 7,403,850 proposed a container made of plastic material provided with individual compartments for accommodating and shipping artificial teeth. This design also is not satisfactory since it is not possible to view and judge sets of anterior and/or lateral teeth as they would appear in a denture, and such as a technician processing artificial teeth has been accustomed to view them. Also, during recent years, the increasing cost of raw material has had an extremely unfavorable affect on the manufacturing costs of tooth cards and thus, has added to the cost of merchandizing artificial teeth mounted thereon.

SUMMARY OF THE INVENTION

According to the present invention, one of the principal objectives is to provide a mount for artificial teeth that obviates the disadvantages referred to above and instead, does not employ wax strips, yet offers a safe retention of the teeth, as well as return of the anterior and/or posterior teeth to the original location in the mount after they have once been removed therefrom, and at the same time permitting perfect optical evaluation of the teeth, while also making it possible to produce such mounts of cards at much lower cost than conventional cards of the type referred to hereinabove.

The foregoing objective is achieved by employing thin walled plastic material and shaping the same into a desired configuration by deep-drawing, by vaccum-forming or stretch-forming the material of adequate stiffness, which is afforded by using hard PVC deep-drawing foil of substantially 0.75 millimeters. Another object of the invention is to provide in the molded card, formed by the above-mentioned procedure, recesses to receive portions of anterior and/or posterior teeth in a manner to display the normally observed surfaces thereof and at the same time, provide on the mount a suitable adhesive, such as a synthetic resin dispersion adhesive placed only in the bottom of the recesses, whereby in conjunction with such adhesive, the shape of the cavities also aids in retaining the teeth therein.

A further object of the invention is to employ a permanent type adhesive, which, while permitting easy removal of teeth from the cavity, nevertheless, has securing properties essentially greater than possessed by conventional wax heretofore employed and also allowing easy readhesion of the teeth to said adhesive by lightly pressing the same in place within the cavities complementary thereto.

Details of the foregoing objects and of the invention, as well as other objects thereof, are set forth in the following specification and illustrated in the accompanying drawing comprising a part thereof.

DETAILED DESCRIPTION

Figure 1:
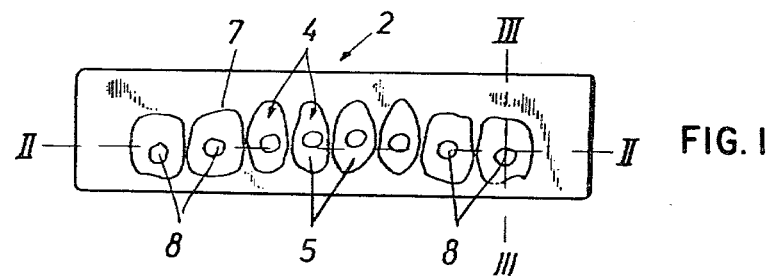
FIG. 1 is a top plan view of a mount embodying the principles of the present invention and designed to hold a set of posterior artificial teeth.
Figure 2:
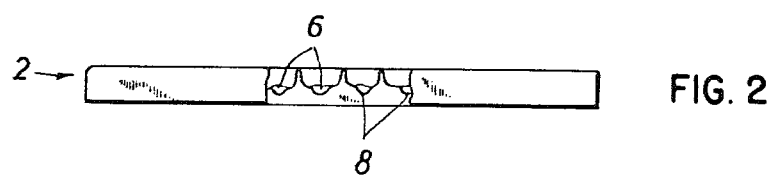
FIG. 2 is a front elevation of the mount shown in FIG. 1 in which a portion of the sidewall has been removed to disclose details of the mount.
Figure 3:
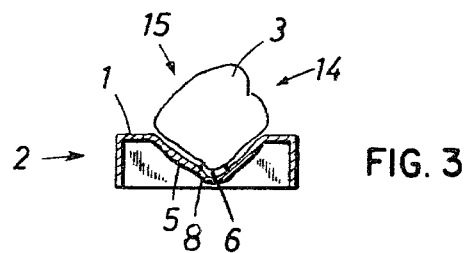
FIG. 3 is a transverse sectional view of the mount shown in FIG. 1, as seen on the line III—III thereof, and illustrating a posterior tooth positioned in the recess therefor in the mount.
Figure 4:
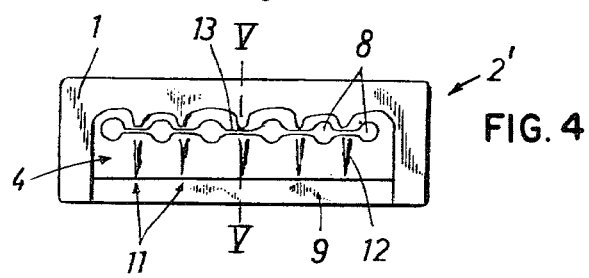
FIG. 4 is a top plan view of a mount embodying the principles of the present invention and especially designed to hold a set of anterior artificial teeth.
Figure 5:
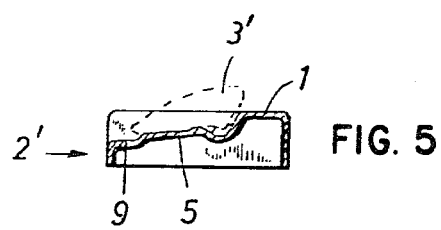
FIG. 5 is a vertical sectional view of the mount shown in FIG. 4, as seen on the line V—V thereof.

The shape of the mount 2 shown in FIGS. 1-3 is especially designed to accommodate a set of posterior teeth 3, while the shape of the mount 2' shown in FIGS. 4 and 5 is designed for holding anterior teeth, comprising incisors. The recesses 4 formed in the upper surface 1 of the mount 2 are provided with bottom surfaces 5 in which placement cups 8 are molded to provide indentations to receive special adhesive, as shown in FIG. 3, and thereby minimize the amount of wax needed to secure teeth to the mount. If desired, the cups 8 may be interconnected by small cross-channels 13, shown in FIG. 4, and in which the top of said channels are open so that the adhesive 6 may be applied at a single location and then will flow sideways for reception in the other cups 8.

In regard to displaying the posterior teeth 3, shown in FIG. 3, it is preferable to present the design of the same so that the mastication surface 14 is observable, as well as the outer faces 15 thereof. To accomplish this, the bottom 5 of the recesses 4 are sloped, as shown in FIG. 3, and because of the face 15 of the posterior tooth 3 being uppermost, the cup 8 is located in the lower gusset and the adhesive 6 is only disposed in said cup.

As is visible in FIG. 3, the tooth 3 is seated in its recess in a way tilted relative to the surface 1 so that it may be removed, when desired, from the relatively small adhesion spot 6, which is completely covered by the tooth. On the other hand, the tooth can be repositioned in the mount easily, which, in a way, is facilitated by the recess and readherence of the tooth to the adhesive only necessitates a light pressing of the tooth in place. The same design would, of course, be applicable to the anterior teeth in the embodiments shown in FIGS. 4 and 5 by changing the form somewhat to correspond to that of the anterior teeth, as shown especially in FIGS. 4 and 5.

It is preferred, however, to design the mounts of the embodiment shown in FIGS. 4 and 5 with the bottoms 5 of the recesses having a grip ledge 9 which opens toward the front of the mount 2' and the anterior teeth 3', shown in phantom in FIG. 5, being seated in the recess in the manner shown in said figure. Detaching the teeth 3', therefore, is easily accomplished from the incisal side, engaging the tooth from below with a fingernail and, on the other hand, lightly pressing the edge of the tooth neck, which is located higher and protrudes somewhat and thereby causes the tooth 3 to slide toward the grip ledge 9, as can be visualized from FIG. 5.

For front observation of a complete set of anterior teeth, possibly small gaps should be provided between the teeth to conform to natural conditions and the recesses therefor within the neighboring areas 11, as shown in FIG. 4, can be separated by a ridge 12, which is located lower than the surface 1 of the mount. By the incorporation of these small separators 12, return of the teeth to their original position in the recesses is assured.

Figure 6:
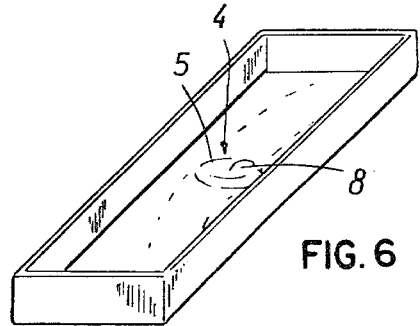
FIG. 6 is a perspective view of the shell-like configuration of the mounts shown in the preceeding figures, as seen from the bottom thereof.

As shown especially in FIG. 6, the complete mount 2 or 2' has advantageously been designed as thin-walled in the form of a flat box-type unit 10, shown from the open bottom thereof in said figure. This mount is produced in a single process, including all recesses, of which only one is indicated in FIG. 6, by using respective molds and specific shapes, from a plastic foil which is sufficiently stiff and moldable that the flat box formed therefrom strengthens the mold additionally. Of course, the mount can also be made in the shape of a small block made of solid material of which the surface 1 is provided with recesses 4 in the form of hollows. If using solid material, in particular materials that can be cast or die-cast, it is appropriate that the mount can be formed in one piece, after the respective mold has been prepared for such purpose.

The flat box formed, shown in FIG. 6, does, of course, not exclude the possibility that the whole unit, respectively the mount, can also be arc-shaped in which the surface 1 would be in the form of an arc and approximately in the sense of the natural jaw curvature.

Furthermore, it will also be possible to accommodate in one mount both anterior and posterior recesses, the anterior recesses being in the center, followed by the posteriors on either side thereof.

A further design, not shown, would be for the surface 1 to have the shape of a roof, that is, two surfaces forming an angle and each surface being provided with a row of recesses.

In connection with the recesses 4, it is also indicated that their form and contour can be so that only teeth of slightly different size, but of same type, can be inserted. Accordingly, the manufacture of artificial teeth only requires a relatively low number of sizes of mounts, that is, only for small and large teeth of tooth sets.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. A mount for a set of artificial teeth comprising an elongated base member provided with a forward edge and a series of concave recesses conforming respectively to a portion of an artificial tooth of said set thereof and complementary in shape to said surfaces, and indentations formed in the bottoms of said recesses respectively having a small quantity of tacky adhesive substantially restricted to said indentation therein adapted to releasably engage part of said surface portions of said teeth to retain the teeth in said recesses in a manner to display the same visually for instant observation.

2. The mount according to claim 1 further including cross channels extending longitudinally along said base member and transversely between midportions of said indentations for said adhesive to facilitate the placement of adhesive in said indentations.

3. The mount according to claim 1 in which said base member has an upper horizontal surface portion extending outward from and adjacent the plane of the forward edge of said recesses at a slightly lower level than the adjacent forward portion of each recess to serve as an access ledge to facilitate removing teeth from said recesses by prying the forward edges of the teeth manually upward.

4. The mount according to claim 1 further including upstanding separating ridges between adjacent recesses to facilitate mounting said teeth accurately and respectively in said recesses.

* * * * *